United States Patent [19]

Desobry et al.

[11] Patent Number: 5,247,107

[45] Date of Patent: * Sep. 21, 1993

[54] PROCESS FOR THE PREPARATION OF ORGANOMETALLIC COMPOUNDS

[75] Inventors: Vincent Desobry, Marly; Hans O. Doggweiler, Möhlin, both of Switzerland

[73] Assignee: Ciba-Geigy Corporation, Ardsley, N.Y.

[*] Notice: The portion of the term of this patent subsequent to Feb. 12, 2008 has been disclaimed.

[21] Appl. No.: 809,216

[22] Filed: Dec. 16, 1991

Related U.S. Application Data

[63] Continuation of Ser. No. 620,242, Nov. 29, 1990, abandoned, which is a continuation of Ser. No. 258,544, Oct. 17, 1988, Pat. No. 4,992,572.

[30] Foreign Application Priority Data

Oct. 26, 1987 [CH] Switzerland .................. 4203/87

[51] Int. Cl.$^5$ ............................. C07F 7/28
[52] U.S. Cl. ................... 556/52; 556/53; 556/140; 556/144
[58] Field of Search .............. 556/52, 53, 140, 143, 556/144

[56] References Cited

U.S. PATENT DOCUMENTS 4,973,722  11/1990  Doggweiler et al. .......... 556/143
4,992,572  2/1991  Desobry et al. ............. 556/143

FOREIGN PATENT DOCUMENTS 577738  6/1959  Canada ..................... 556/143

OTHER PUBLICATIONS

Nesmayanov Khoord. Khim. 1 1252 (1975).
Translation of Koord. Khim., vol. 1, p. 125 (1975).
Chemiker Zeitung. vol. 108 (7/8) p. 239-251 (1984).
Journal of Organometallic Chem. vol. 111 pp. 339-347 (1976).

*Primary Examiner*—Michael Lewis
*Assistant Examiner*—Stuart L. Hendrickson
*Attorney, Agent, or Firm*—JoAnn Villamizar

[57] ABSTRACT

There is disclosed a process for the preparation of compounds of formula I $$[R\ Fe\ R^2]_q^{\oplus} X^{q\ominus} \qquad (I),$$

wherein R is an anion of formula $C_5H_4R^1$ or $C_9H_7$, $R^1$ is hydrogen, $C_1$–$C_6$-alkyl or halogen $R^2$ is a $\pi$-arene, X is an anion of valency q and q is 1, 2 or 3, by reacting ferrocene or a ferrocene derivative $(C_5H_4R^3)Fe(C_5H_4R^1)$ or $(C_9H_7)_2Fe$, in which $R^3$ has one of the meanings of $R^1$, with at least one mole of a $\pi$-arene $R^2$, followed by the optional replacement of the anion $X^{q\ominus}$ in a manner known per se, the reaction of the ferrocene or ferrocene derivative being carried out in the presence of a) at least 1.2 mol of a mixture of Al trihalide and Zr(IV) or Hf(IV) tetrahalide, in the presence or absence of a metallic reducing agent, such that at least 0.2 mol of Zr(IV) or Hf(IV) tetrahalide and at least 0.1 mol of Al trihalide are present, or of b) at least 1.0 mol of a Zr(IV) or Hf(IV) tetrahalide as sole Lewis acid in conjunction with at least 1.0 mol of a metallic reducing agent, the amounts being based in each case on 1 mol of ferrocene or a ferrocene derivative.

The compounds of formula I containing non-nucleophilic anions can be used as photoinitiators for cationically polymerisable compounds.

5 Claims, No Drawings

PROCESS FOR THE PREPARATION OF ORGANOMETALLIC COMPOUNDS

This application is a continuation of application Ser. No. 620,242, filed Nov. 29, 1990 now abandoned which in turn is a continuation of Ser. No. 258,544 filed Oct. 17, 1988, now U.S. Pat. No. 4,492,572.

The present invention relates to an improved process for the preparation of organometallic compounds, in particular of iron-arene complexes, by ligand exchange reaction with ferrocene or a ferrocene derivative.

Iron-arene complexes and the use thereof as photoinitiators for cationically polymerisable materials are known and described for example in EP-A-94 915. In general, the compounds are prepared from metallocene compounds by ligand exchange reactions. To this end, the metallocene compound, for example ferrocene, is reacted with an aromatic compound in the presence of a Lewis acid and Al metal.

The preparation of cyclopentadiene-iron-arene compounds is described for example in Chemiker Zeitung 108 (7/8), 239 (1984) and 108 (11). 345 (1984). Further examples of these reactions are found in Koord. Khim., 1, 1252 (1975).

The Lewis acids used in these reactions are, for example, Al halides, $ZrCl_4$ and $HfCl_4$.

It has now been found that high yields of iron-arene complex salt are obtained by using a mixture of Al trihalide and Zr(IV) or Hf(IV) tetrahalide as Lewis acid, or by using a combination of these Zr(IV) or Hf(IV) compounds with a metallic reducing agent.

In addition, it is sometimes possible to obtain two useful organometallic compounds simultaneously by careful choice of the amounts of reactants.

In this reaction, the property of the Zr(IV) or Hf(IV) halide as acceptor for the exchanged cyclopentadiene or derivative thereof is exploited to give in the cited instances a reaction product that can be isolated. In carrying out the ligand exchange with $AlCl_3$, polymeric products are normally formed from the leaving cyclopentadiene or derivative thereof (cf. D. Astruc et al. in Tetrahedron, 32, 245-249 (1976)).

The present invention relates to a process for the preparation of compounds of formula I

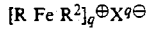     (I), wherein R is an anion of formula $C_5H_4R^1$ or $C_9H_7$, $R^1$ is hydrogen, $C_1$–$C_6$-alkyl or halogen, $R^2$ is a π-arene, X is an anion of valency q and q is 1, 2 or 3, by reacting ferrocene or a ferrocene derivative $(C_5H_4R^3)Fe(C_5H_4R^1)$ or $(C_9H_7)_2Fe$, in which $R^3$ has one of the meanings of $R^1$, with at least one mole of a π-arene $R^2$, followed by the optional replacement of the anion $X^{q\ominus}$ in a manner known per se, the reaction of the ferrocene or ferrocene derivative being carried out in the presence of a) at least 1.2 mol of a mixture of Al trihalide and Zr(IV) or Hf(IV) tetrahalide, in the presence or absence of a metallic reducing agent, such that at least 0.2 mol of Zr(IV) or Hf(IV) tetrahalide and at least 0.1 mol of Al trihalide are present; or of b) at least 1.0 mol of a Zr(IV) or Hf(IV) tetrahalide as sole Lewis acid in conjunction with at least 1.0 mol of a metallic reducing agent, the amounts being based in each case on 1 mol of ferrocene or a ferrocene derivative.

The index q is preferably 1 or 2, most preferably 1. R is an indenyl anion $C_9H_7$ or, preferably, a cyclopentadienyl anion $C_5H_4R^2$.

$R^1$ and $R^3$ as $C_1$–$C_6$alkyl are straight chain or branched, preferably straight chain. Examples of such radicals are: methyl, ethyl, n-propyl, isopropyl, n-butyl, n-pentyl or n-hexyl. Methyl is preferred.

$R^1$ and $R^3$ as halogen are fluorine, chlorine, bromine or iodine. Chlorine is preferred.

$R^1$ and $R^3$ are preferably hydrogen or methyl. Hydrogen is particularly preferred.

Particularly suitable π-arenes $R^2$ are aromatic hydrocarbons containing 6 to 24 carbon atoms or heterocyclic-aromatic hydrocarbons containing 3 to 30 carbon atoms and one or two hetero atoms, which groups may be substituted by one or more identical or different monovalent radicals such as halogen atoms, preferably chlorine or bromine atoms, or $C_1$–$C_8$alkyl, $C_1$–$C_8$alkoxy, cyano, $C_1$–$C_8$alkylthio, $C_2$–$C_6$alkanoyl or phenyl groups. These π-arene groups can be mononuclear, fused polynuclear or non-fused polynuclear systems, the nuclei in which last mentioned systems may be linked direct or through bridge members, for example $-CH_2-$, $-CO-$, $-O-$, $-S-$ or $-SO_2-$.

Suitable heteroaromatic π-arenes are systems which preferably contain one or two S and/or O atoms.

Examples of suitable π-arenes are benzene, toluene, xylenes, ethylbenzene, cumene, methoxybenzene, ethoxybenzene, dimethoxybenzene, p-chlorotoluene, m-chlorotoluene, chlorobenzene, bromobenzene, dichlorobenzene, diisopropylbenzene, trimethylbenzene, naphthalene, 1,2-dihydronaphthalene, 1,2,3,4-tetrahydronaphthalene, methylnaphthalene, methoxynaphthalene, ethoxynaphthalene, chloronaphthalene, bromonaphthalene, dimethylnaphthalene, biphenyl, stilbene, indene, 4,4'-dimethylbiphenyl, fluorene, phenanthrene, anthracene, 9,10-dihydroanthracene, triphenyl, pyrene, perylene, naphthacene, coronene, thiophene, chromene, xanthene, thioxanthene, benzofuran, benzothiophene, naphthothiophene, thianthrene, diphenylene oxide and diphenylene sulfide.

X can be any q-valent anion of an inorganic or organic acid, for example a halide, i.e. fluoride, chloride, bromide or iodide, or a pseudohalide, for example cyanide, cyanate or thiocyanate, or an anion of other inorganic acids, for example sulfate, phosphate, nitrate, perchlorate or tetraphenylborate.

Further suitable anions are derived from sulfonic acids of aliphatic or aromatic compounds. Preferred examples thereof are p-toluenesulfonate, p-trifluoromethylbenzenesulfonate and trifluoromethylsulfonate.

Non-nucleophilic anions $X^{q\ominus}$ are especially preferred.

Suitable non-nucleophilic anions $X^{q\ominus}$ are preferably anions of formula II

     (II), in which L is a di- to heptavalent metal or non-metal, Q is a halogen atom, preferably fluorine, or, if L is phosphorus, arsenic or antimony and m is 5, can additionally be OH, q is 1, 2 or 3 and m is an integer corresponding to the valency of L+q.

Examples of such anions are $BF_4^-$, $AlF_4^-$, $AlCl_4^-$, $TiF_6^{2-}$, $PF_6^-$, $SbF_6^-$, $SbCl_6^-$, $SbF_5(OH)^-$, $GeF_6^-$, $ZrF_6^{2-}$, $AsF_6^-$, $FeCl_4^-$, $SnF_6^{2-}$, $SnCl_6^{2-}$ and BiCl$_6^-$. Preferred examples of complex anions are BF$_4^-$, and in particular AsF$_6^-$, SbF$_6^-$ and PF$_6^-$.

The above defined Al trihalides or Zr(IV) of Hf(IV) tetrahalides include the corresponding chlorides, bromides or iodides. It is preferred to use the chlorides or bromides, but most preferably the chlorides.

Preferred Zr(IV) or Hf(IV) tetrahalides are ZrBr$_4$ or HfBr$_4$ and, in particular, ZrCl$_4$ or HfCl$_4$. The preferred Al trihalide is AlCl$_3$, especially sublimed AlCl$_3$.

The preferred total amount of Lewis acid in variant a) is 1.2 to 4.0 mol, especially 1.6 to 2.0 mol and, most preferably, 1.7 to 1.9 mol, based on 1 mol of ferrocene or ferrocene derivative.

The preferred amount of Zr(IV) or Hf(IV) tetrahalide in variant b) is 1.0 to 3.0 mol, most preferably 1.5 to 2.0 mol, based on 1 mol of ferrocene or ferrocene derivative.

The molar ratio of Zr(IV) or Hf(IV) tetrahalide to Al trihalide in variant a) is preferably 1:4 to 4:1, most preferably 1:2 to 1:3.

Examples of metallic reducing agents are magnesium, zinc or aluminium. Aluminium is particularly preferred.

The embodiment wherein a mixture of Zr(IV) or Hf(IV) tetrahalide/Al trihalide containing 0.3–0.7 mol, preferably 0.4–0.6 mol, most preferably about 0.5 mol, of the appropriate (IV) halide, based on 1 mol of ferrocene or ferrocene derivative, in conjunction with a metallic reducing agent, is particularly preferred, as this process results, in addition to the metallocene derivative of formula I, in the formation of the product of formula III

(R)$_2$M(Hal)$_2$         (III)

wherein R is as defined above, preferably C$_5$H$_4$R$^1$, M is Zr or Hf, and Hal is a halogen atom.

Compounds of formula III are valuable intermediates for organic syntheses. Their use is described, for example, in J. Organomet. Chemistry, 290. C4–C6 (1985).

In the above variant, the property of the Zr(IV) or Hf(IV) halide as cyclopentadienyl acceptor is exploited. The cyclopentadienyl or derivative thereof replaced in the ferrocene or ferrocene derivative is thus transferred to the Zr(IV) or Hf(IV) halide.

In this variant, it is expedient to choose a molar ratio of Al trihalide to the appropriate (IV) halide of 2:1 or greater than 2:1.

Amounts of Zr(IV) of Hf(IV) halide far in excess of the stoichiometric amounts should be avoided in this process variant, as otherwise polymeric by-products may form that lead to a reduction in yield of (Cpd)$_2$MHal$_2$ [Cpd=cyclopentadienyl anion] and that can result in problems during working up (filtration).

In this process variant it is preferred to use a mixture of 0.3–0.7 mol of Zr(IV) or Hf(IV) tetrahalide and 0.8–2.0 mol of Al trihalide, based on 1 mol of ferrocene or ferrocene derivative, together with finely particulate aluminium. Halide in this variant denotes bromide or chloride.

It is especially preferred in this process variant to use a mixture of 0.4–0.6 mol of Zr(IV) or Hf(IV) tetrahalide and 1.0–1.8 mol of Al trihalide, together with 0.1–1.0 mol of finely particulate aluminium, based on 1 mol of ferrocene or ferrocene derivative. Halide in this variant denotes bromide or chloride.

A further particularly preferred embodiment of the process comprises using a mixture of 0.4–0.6 mol, preferably about 0.5 mol, of ZrCl$_4$ or HfCl$_4$ and 1.2–1.4 mol, preferably 1.3–1.35 mol, of AlCl$_3$, together with 0.15–0.2 mol of finely particulate aluminium, based on 1 mol of ferrocene or ferrocene derivative.

In this embodiment it is preferred to use the metallic reducing agent in an equivalent amount with respect to the Zr(IV) of Hf(IV) tetrahalide. If the metallic reducing agent is Al, then one third of the molar amount of the Zr(IV) or Hf(IV) tetrahalide will preferably be used.

In the event that variant a) is carried out with an excess or a less than equivalent amount of Zr(IV) or Hf(IV) tetrahalide, it is advisable to add a metallic reducing agent to increase the yield. This reducing agent can be added in any desired amount, though preferably in an amount of more than 0.1 mol, most preferably 0.1 to 1.0 mol, based on 1 mol of ferrocene or ferrocene derivative.

In process variant b), a metallic reducing agent, preferably aluminium metal, must be present. In this embodiment of the process, it is preferred to use 1.0 to 2.0 mol, in particular 1.0 to 1.5 mol, of reducing agent, based on 1 mol of ferrocene or ferrocene derivative.

The metal should be used in a form having a large surface area. It may therefore be added in the form of a metal foil or in finely particulate form, preferably as powder or dust.

The $\pi$-arene can be used in any desired excess, for example as solvent. It should, however, be present in an amount of at least 1 mol, based on 1 mol of ferrocene or ferrocene derivative. Mixtures of $\pi$-arenes may also be used.

The reaction may be carried out in a further solvent. It is possible to use any solvent which is inert under the reaction conditions. The basicity of this solvent should not be so high as to deactivate the Lewis acid or acids excessively. Examples of suitable solvents are aliphatic or cycloaliphatic or aromatic hydrocarbons that may carry non-basic substituents, for example halogen atoms or alkyl groups. Hydrocarbons of 6 to 12 carbon atoms are preferred.

Examples of preferred solvents of this kind are n-hexane, n-heptane, n-octane, n-nonane, n-decane, n-undecane, n-dodecane and corresponding branched representative of these types. It is also possible to use mixtures of aliphatic hydrocarbons, for example the octane fraction. The preferred cycloaliphatic solvent is methylcyclohexane. The aliphatic hydrocarbons can be chlorinated. Further preferred solvents are benzene, toluene, xylene, ethylbenzene, cumene, chlorobenzene and dichlorobenzene.

It is preferred to carry out the reaction without an additional solvent and to use the $\pi$-arene R$^2$ in an amount of 2.0–10.0 mol, based on 1 mol of ferrocene or ferrocene derivative.

The reaction mixture can contain small amounts of water, for example 0.1–2% by weight, based on the amount of Lewis acid, as described for the use of AlCl$_3$ as Lewis acid in Koord. Khim., 1, 1252 (1975).

The ferrocene or ferrocene derivative is preferably ferrocene itself. However, it is also possible to use any desired derivatives which have substituted cyclopentadienyl anions or indenyl anions. Examples of such derivatives are bis(indenyl)iron(II), chloroferrocene, dichloroferrocene, methylferrocene and dimethylferrocene. It is preferred to use ferrrocene and the readily accessible monosubstituted ferrocene derivatives, but in particular ferrocene.

The reaction is conveniently carried out in the temperature range from 15°-250° C. The preferred temperature range is 50°-120° C.

The reaction time is in general 0.25-24 hours, depending on the temperature. Preferably, it is 1-2 hours.

The process can be carried out in air or under an inert gas. It is preferably carried out in the absence of oxygen, for example under nitrogen or under argon.

All the educts can be charged to the reactor, and the reaction can be initiated by heating. In some cases, however, it may be expedient to add individual reactants during the reaction. For example, $ZrCl_4$ or $HfCl_4$ can be added during the reaction to control the reaction rate and hence also the heat of reaction.

Upon completion of the reaction, the reaction mixture is in general deactivated with water or a mixture of ice-water which may be acidified. Thereafter the mixture is usually filtered to remove Al metal or undissolved reactants. It may additionally be necessary to effect phase separation. The aqueous phase may then be extracted with a polar, organic solvent, for example with chloroform or dichloromethane, to remove unconverted compounds or useful by-products. This extraction step is of particular interest in the reaction variant in which $R_2M(Hal)_2$ is formed simultaneously. In this case, deactivation is effected with acidified water or a mixture of ice-water, and filtration and phase separation are followed by extraction with an organic polar solvent.

The compound of formula I is initially obtained in the form of the halide. This halide is, if desired, isolated and purified in a manner known per se, for example by recristallisation, or other anions are introduced in a manner known per se in that course of working up the reaction mixture. For example, an acid or a water-soluble salt of said acid can be added to the isolated aqueous phase to precipitate the compound of the formula I.

Examples of suitable precipitants are the Na or K salts and the free acids of the anions listed above as preferred.

These anions can also be introduced in a manner known per se by means of ion exchange.

The compounds of formula I containing non-nucleophilic anions can be used as photoinitiators for cationically polymerisable materials. Compounds of formula I with nucleophilic anions can be used for preparing these photoinitiators in the manner described above.

The invention is illustrated by the following Examples.

EXAMPLE 1

($\eta^6$-Mesitylene)-($\eta^5$-cyclopentadienyl)-iron(II) hexafluorophosohate 10 g (0,043 mol) of zirconium tetrachloride are added at 60° C. over 30 minutes under nitrogen to a stirred mixture of 8 g (0.043 mol) of ferrocene, 10 g (0.043 mol) of zirconium tetrachloride and 1,2 g (0.043 mol) of aluminium powder in 50 ml (0.43 mol) of mesitylene. The reaction mixture is heated to 100° C. and kept at this temperature for 2 hours, then cooled, and a solution of 16 ml of 32 % HCl in 85 ml of water is slowly added dropwise. After 15 minutes the mixture is filtered over Hyflo (filter aid), the two phases are separated, and the aqueous phase is added to a solution of 8.7 g (0.047 mol) of $KPF_6$ in 100 ml of water.

Filtration and drying yield 12.1 g (72.9% of theory) of crude ($\eta^6$-mesitylene)-($\eta^5$-cyclopentadienyl)-iron(II) $PF_6$ which melts at 210°-220° C. (dec). Crystallisation from ethanol: 51% of theory; m.p.: 269° C. (dec).

EXAMPLE 2

A mixture of 8 g (0.043 mol) of ferrocene, 9 g (0.0386 mol) of $ZrCl_4$, 0.6 g (0.0043 mol) of $AlCl_3$, 50 ml (0.43 mol) of mesitylene and 1.2 g (0.043 mol) of Al powder are charged at 60° C. under $N_2$ to a reactor and then 10 g (0.043 mol) of $ZrCl_4$ are slowly added at 60° C. The reaction mixture is heated to 100° C. and kept for 2 hours at this temperature. Working up as in Example 1 affords 12.6 g of crude ($\eta^6$-mesitylene)-$\eta^5$-(cyclopentadienyl)-iron(II) $PF_6$ (81.9% of theory) which melts at 215°-230° C. Crystallisation from ethanol: 43.5 % of theory; m.p.: 269° C. (dec.).

EXAMPLE 3

A mixture of 8 g (0.043 mol) of ferrocene, 5.7 g (0.043 mol) of $AlCl_3$ and 60 ml (0.5 mol) of mesitylene are charged at 60° C. under $N_2$ to a reactor and then, at this temperature, 2 g (0.0086 mol) of $ZrCl_4$ are added over 30 minutes. The mixture is heated for 2 hours to 100° C., then cooled, and a mixture of 60 ml of dichloromethane and 15 ml of a 32% solution of HCl are added dropwise. Then 200 ml of water are added and the batch is filtered. After phase separation, the aqueous phase is washed with 3×50 ml of dichloromethane and added to a solution of 16.2 g (0.0473 mol) of sodium tetraphenylborate in 200 ml of water. Filtration and drying yield 13.9 g (57.6% of theory) of crude product (m.p. 229°-237° C.).

EXAMPLE 4

A mixture of 8 g (0.043 mol) of ferrocene (crystallised from toluene), 5.7 g (0.043 mol) of sublimed $AlCl_3$ and 60 ml (0.5 mol) of mesitylene (distilled over sodium) are charged at 60° C. under argon to a reactor and then, at this temperature, 2 g (0.0086 mol) of $ZrCl_4$ are added over 60 minutes. The mixture is heated for 2 hours to 100° C., then cooled, and a mixture of 60 ml of dichloromethane and 15 ml of a 32% solution of HCl are added dropwise. Then 200 ml of water are added and the batch is filtered. After phase separation, the aqueous phase is washed with 3×80 ml of dichloromethane and added to a solution of 16.2 g (0.0473 mol) of sodium tetraphenylborate in 200 ml of water.

Filtration and drying yield 15.35 g (63.9% of theory) of crude product. Precipitation from a concentrated acetone solution on addition of ether yields 7.65 g (31.85% of theory) of purified ($\eta^6$-mesitylene)-($\eta^5$-cyclopentadienyl)-iron(II) tetraphenylborate which melts at 268° C.

EXAMPLE 5

17.5 g (0.075 mol) of zirconium tetrachloride are added at 60° C. under nitrogen over 30 minutes to a stirred mixture of 129.7 g (1.265 mol) of cumene, 27.9 g (0.15 mol) of ferrocene, 26.6 g (0.199 mol) of aluminium chloride and 0.7 g (0.025 mol) of aluminium powder. The reaction mixture is heated and then stirred for 1.5 hours at 110° C., cooled to 25° C., and then slowly poured into a cold mixture of −10° C. of 200 ml of dichloromethane and 50 ml of 32% hydrochloric acid. The mixture is then diluted with a further 200 ml of 5% hydrochloric acid under nitrogen and the two phases are separated. The lower dichloromethane phase containing zirconocene dichloride is concentrated by rotary evaporation and the residual solid is dried under a high vacuum, affording 13 g of zirconocene dichloride [59.4% of theory, sublimed 50.5%, m.p. 195° C. (dec.)].

Analysis: cal. (%) C 41.09, H 3.45, Cl 24.26. found (%) C 41.19, H 3.54, Cl 24.17.

The upper, aqueous phase is treated with 30.4 g (0.165 mol) of potassium hexafluorophosphate and the precipitated ($\eta^6$-cumene)-($\eta^5$-cyclopentadienyl)-iron(II) PF$_6$ is isolated by filtration, washed and dried.

Yield: 52.4 g (90.5% of theory; m.p.: 80°–84° C.).

Analysis: cal. (%) C 43.35, H 4.44. found (%) C 43.38, H 4.42.

EXAMPLE 6

In accordance with the procedure of Example 5, 4.3 g (0.0134 mol) of hafnium tetrachloride are added at 55° C. under nitrogen over 30 minutes to a stirred mixture of 56 g of cumene, 5 g (0.027 mol) of ferrocene, 4.8 g (0.0358 mol) of aluminium chloride and 0.12 g (0.0045 mol) of aluminium powder. Working up is effected as in Example 4, affording 3.5 g (68.6% of theory) of hafnocene dichloride which melts at 228°–230° C.

UV spectrum in CHCl$_3$: $\lambda_{max}$ ($\epsilon$) 266.4 nm (2.751) 306.3 nm (0.714).

Analysis cal. (%) C 31.64, H 2.66, Cl 18.68. found. (%) C 33.25, H 2.91, Cl 18.30.

The yield of ($\eta^6$-cumene)-($\eta^5$-cyclopentadienyl)-iron-(II) PF$_6$ is 5.7 g (58% of theory). Melting point: 83°–85° C.

EXAMPLE 7

In accordance with the procedure of Example 4, 10 g (0.043 mol) of ZrCl$_4$ are added at 60° C. under argon over the course of 1 hour and 10 minutes to a stirred mixture of 60 ml of mesitylene, 8 g (0.043 mol) of ferrocene and 5.7 g (0.043 mol) of sublimed AlCl$_3$. Working up is effected as in Example 4, affording 20.1 g (83.4% of theory) of crude ($\eta^6$-mesitylene)-$\eta^5$-(cyclopentadienyl)-iron(II) tetrapnenylborate.

Precipitation from a concentrated solution of acetone by addition of ether yields 45.0% of purified product which melts at 268° C.

What is claimed is:

1. A process for the preparation of a compound of formulae I and III $$[RFe\ R^2]_q^+ X^{q-} \qquad (I)$$

$$(R)_2(M(Hal)_2 \qquad (III),$$

wherein R is an anion of formula C$_5$H$_4$R$^1$ or C$_9$H$_7$, R$^1$ is hydrogen, C$_1$–C$_6$-alkyl or halogen, R$^2$ is a $\pi$-arene, X is an anion of valence q and q is 1, 2, or 3, M is Zr or Hf and Hal is a halogen atom, by reacting ferrocene or a ferrocene derivative (C$_5$H$_4$R$^3$)Fe(C$_5$H$_4$R$^1$) or C$_9$H$_7$)$_2$Fe, in which R$^3$ has one of the meanings of R$^1$, with at least one mole of a $\pi$-arene R$^2$ in the presence of at least 1.2 mol of a mixture of 0.3–0.7 mol of Zr(IV) tetrahalide and 0.8–2 mol of Al trihalide or a mixture of 0.3–0.7 mole of Hf(IV) tetrahalide and 0.8–2.0 mol of Al trihalide, such that at least 0.2 mol of Zr(IV) tetrahalide or Hf(IV) tetrahalide and at least 0.1 mol of Al trihalide are present, based on 1 mol of ferrocene or ferrocene derivative and a metallic reducing agent.

2. A process according to claim 1, which comprises using a mixture of 0.3–0.7 mol of Zr(IV) tetrahalide and 0.8–2.0 mol of Al trihalide or a mixture of 0.3–0.7 mol of Hf(IV) tetrahalide and 0.8–2.0 mol of Al trihalide, based on 1 mol of ferrocene or ferrocene derivative, together with finely particulate aluminum, and wherein said halide is bromide or chloride.

3. A process according to claim 1, which comprises using a mixture of 0.4–0.6 mol of Zr(IV) tetrahalide and 1.0–1.8 mol of Al trihalide or a mixture of 0.4–0.6 mol of Hf(IV) tetrahalide and 1.0–1.8 mol of Al trihalide, together with 0.1–1.0 mol of finely particulate aluminum, based on 1 mol of ferrocene or ferrocene derivative, and wherein said halide is bromide or chloride.

4. A process according to claim 1, wherein the Lewis acid is a mixture of 0.4–0.6 mol of ZrCL$_4$ and 1.2–1.4 mol of AlCl$_3$ or a mixture of 0.4–0.6 mol of HfCl$_4$ and 1.2–1.4 mol of AlCl$_3$, together with 0.15–0.2 mol of finely particulate aluminum, based on 1 mol of ferrocene or ferrocene derivative.

5. A process according to claim 1, wherein the reaction mixture, after completion of the reaction, is deactivated with acidified water or a mixture of ice and water and, after filtration and phase separation, the aqueous phase is extracted with an organic polar solvent.

* * * * *